(12) United States Patent
Thirman

(10) Patent No.: US 8,557,778 B2
(45) Date of Patent: *Oct. 15, 2013

(54) THERAPEUTICS TO INHIBIT MLL-MENIN INTERACTION FOR TREATING LEUKEMIA

(75) Inventor: Michael J. Thirman, Wilmette, IL (US)

(73) Assignee: The University of Chicago, Chicago, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/552,126

(22) Filed: Jul. 18, 2012

(65) Prior Publication Data

US 2012/0322742 A1     Dec. 20, 2012

Related U.S. Application Data

(63) Continuation of application No. 12/446,206, filed as application No. PCT/US2007/081997 on Oct. 19, 2007, now Pat. No. 8,242,078.

(60) Provisional application No. 60/862,067, filed on Oct. 19, 2006.

(51) Int. Cl.
*A61K 38/00* (2006.01)

(52) U.S. Cl.
USPC .......................................................... 514/19.2

(58) Field of Classification Search
None
See application file for complete search history.

(56) References Cited

U.S. PATENT DOCUMENTS 8,242,078 B2 *   8/2012   Thirman ..................... 514/19.2

* cited by examiner

*Primary Examiner* — Sheela J Huff
(74) *Attorney, Agent, or Firm* — Barnes & Thornburg LLP; Alice O. Martin

(57) ABSTRACT

Cell permeable peptides derived from MLL that block the interaction of MLL with menin for the treatment of acute myeloid and acute lymphoid leukemia are disclosed. Small molecules interfere with the interaction of MLL with any of its binding partners.

6 Claims, 5 Drawing Sheets

THERAPEUTICS TO INHIBIT MLL-MENIN INTERACTION FOR TREATING LEUKEMIA

CROSS REFERENCE TO RELATED APPLICATIONS

This application is a continuation of U.S. Ser. No. 12/446,206 filed Jul. 23, 2009, which is a U.S. nationalization under 35 U.S.C. §371 of International Application No. PCT/US2007/81997 filed Oct. 19, 2007 which claims the benefit of priority under 35 U.S.C. §119(e) to U.S. Provisional Patent Application No. 60/862,067 filed Oct. 19, 2006. The disclosures set forth in the referenced applications are incorporated herein by reference in their entireties, including all information as originally submitted to the United States Patent and Trademark Office.

BACKGROUND

Mixed-lineage leukemia (MLL) is a proto-oncogene that was originally discovered at the site of chromosomal translocations in human leukemias. Due to chromosomal translocations, MLL is fused with more than 40 different partner proteins to yield a diverse collection of chimeric fusion proteins. The MLL protein is a histone methyltransferase that covalently modifies chromatin and is mutated in certain subsets of acute leukemia. Many of the fusion partners constitutively activate novel transcriptional effector properties of MLL that often correlate with its oncogenic potential in animal models of acute leukemia. MLL normally associates with a group of highly conserved cofactors to form a macromolecular complex that includes menin, a product of the MEN1 tumor suppressor gene. The MEN1 gene is mutated in heritable and sporadic endocrine tumors. Overexpression of menin leads to inhibition of Ras-transformed cells. Menin interacts with the transcription factors JunD and NFκB and represses their activation of gene transcription. Studies on these interacting proteins suggest that menin exerts its effects predominantly through inhibitory effects on transcription. However, an alternative possibility is that menin mediates its effects through transcriptional activation of target genes. Additionally, menin interacts with RPA2, a component of a single-stranded DNA-binding protein involved in DNA repair and replication. Menin also interacts with FANCD2, a nuclear protein that plays a critical role in maintaining genome stability with breast cancer 1 gene (Brca1) product.

The exact mechanisms by which menin, which does not have significant homology with other proteins, functions as a tumor suppressor are unknown. Menin plays a role in regulating cellular proliferation because Men1 knockout mice show increased proliferation in neuroendocrine tissues, down-modulation of menin in epithelial cells increases proliferation, and Men1 knockout fibroblasts proliferate more rapidly than wild-type cells as assayed by tritiated thymidine incorporation. MEN1 cells also have increased sensitivity to DNA-damaging agents. Menin interacts with promoters of HOX genes.

Certain oncogenic MLL fusion proteins stably associate with menin through a high-affinity interaction that is required for the initiation of MLL-mediated leukemogenesis. Menin is essential for maintenance of MLL-associated but not other oncogene induced myeloid transformation. Acute genetic ablation of menin reverses Hox gene expression mediated by MLL-menin promoter-associated complexes, and specifically eliminates the differentiation arrest and oncogenic properties of MLL-transformed leukemic blasts.

MLL fusion proteins, a consequence of acquired genetic aberrations, transform hematopoietic cells through two alternate mechanisms, by either constitutive transcriptional effector activity or inducing forced MLL dimerization and oligomerization. Both mechanisms result in the inappropriate expression of a subset of HOX genes, particularly HOXA9, whose consistent expression is a characteristic feature of human MLL leukemias.

Therefore, therapeutic compositions to inhibit interaction of MLL fusion proteins with menin or other MLL binding partners is desired.

SUMMARY

Cell-permeable fusion proteins of mixed-lineage leukemia (MLL) that are capable of inhibiting MLL-menin binding and thereby inducing cell death in leukemia are disclosed. Methods and composition are described for induction of cell death in leukemic cells treated with a cell-permeable TAT-MLL fusion peptide. The Menin and MLL interaction may still be important in the initiation and/or maintenance of leukemia's that fail to exhibit a detectable MLL translocation and/or to express a MLL fusion protein. Consequently, the therapeutic approaches to inhibit MLL-Menin binding described in this application may be useful in the treatment of patients whose leukemias do not exhibit a detectable MLL gene rearrangement and/or MLL fusion protein.

A method of inducing cell death in a malignant hematological cell, includes the steps of:
 (a) providing an agent that disrupts the interaction of mixed-lineage leukemia (MLL) and menin, wherein the agent is capable of interfering with MLL protein binding to menin through a binding region of MLL comprising an amino acid sequence CRWRFPARPG (SEQ ID NO: 14) (designated 5-14 based on amino acid positions of MLL from the N-terminus) and
 (b) inducing cell death in the malignant cell.

A 5-13 peptide is sufficient, but adding a G facilitates synthesis.

A therapeutic composition consisting essentially of a MLL-derived peptide includes a peptide consisting essentially of an amino acid sequence CRWRPFARPG (SEQ ID NO: 14).

Compositions that consist essentially of the MLL-derived peptides disclosed herein may have other amino acid sequences that do not materially affect the inhibitory characteristics of the peptides disclosed herein. Such peptides include for example, cell permeable peptides, sequences that increase the stability or delivery or solubility of the peptides disclosed herein.

Synthetic MLL-derived peptides with specific amino acid boundaries disclosed herein inhibit MLL's interaction with one or more proteins.

Synthetic peptides of MLL can also be synthesized with non-standard amino acids to improve stability (e.g., resistant to protease digestion). Amino-acid analogs can also be used to synthesize MLL-derived peptides to inhibit MLL-interaction both in vitro and in vivo.

A therapeutic composition including an effective amount of a cell-permeable MLL fusion peptide including an amino acid sequence selected from the following sequences (using the single letter designations for amino acids and amino acid numbers from the N-terminus):

1-13     MAHSCRWRFPARP     (SEQ ID NO: 1)

```
                                      (SEQ ID NO: 2)
1-14         MAHSCRWRFPARPG (SEQ ID NO: 3)
1-18         MAHSCRWRFPARPGTTGG (SEQ ID NO: 4)
1-22         MAHSCRWRFPARPGTTGGGGGG (SEQ ID NO: 5)
1-26         MAHSCRWRFPARPGTTGGGGGGGRRG (SEQ ID NO: 6)
1-30         MAHSCRWRFPARPGTTGGGGGGGRRGLGGG (SEQ ID NO: 7)
2-18         AHSCRWRFPARPGTTGG (SEQ ID NO: 8)
3-18         HSCRWRFPARPGTTGG (SEQ ID NO: 9)
4-18         SCRWRFPARPGTTGG (SEQ ID NO: 10)
5-18         CRWRFPARPGTTGG (SEQ ID NO: 11)
2-14         AHSCRWRFPARPG (SEQ ID NO: 12)
3-14         HSCRWRFPARPG (SEQ ID NO: 13)
4-14         SCRWRFPARPG
and (SEQ ID NO: 14)
5-14         CRWRFPARPG.
```

THP-1-MLL-AF9
HRX-ELL-MLL-ELL
MV411—MLL-AF4
RS411-MLL-AF4
HL60—No MLL fusion
U937—MLL-AF10
Mouse#4-NE—Derived from a mouse that received a transplant of bone marrow cells transduced with MLL-ELL. However, this cell line no longer expresses MLL-ELL as by immunofluorescence staining with antibodies to ELL and RT-PCR for the MLL-ELL mRNA.

Figure 6:
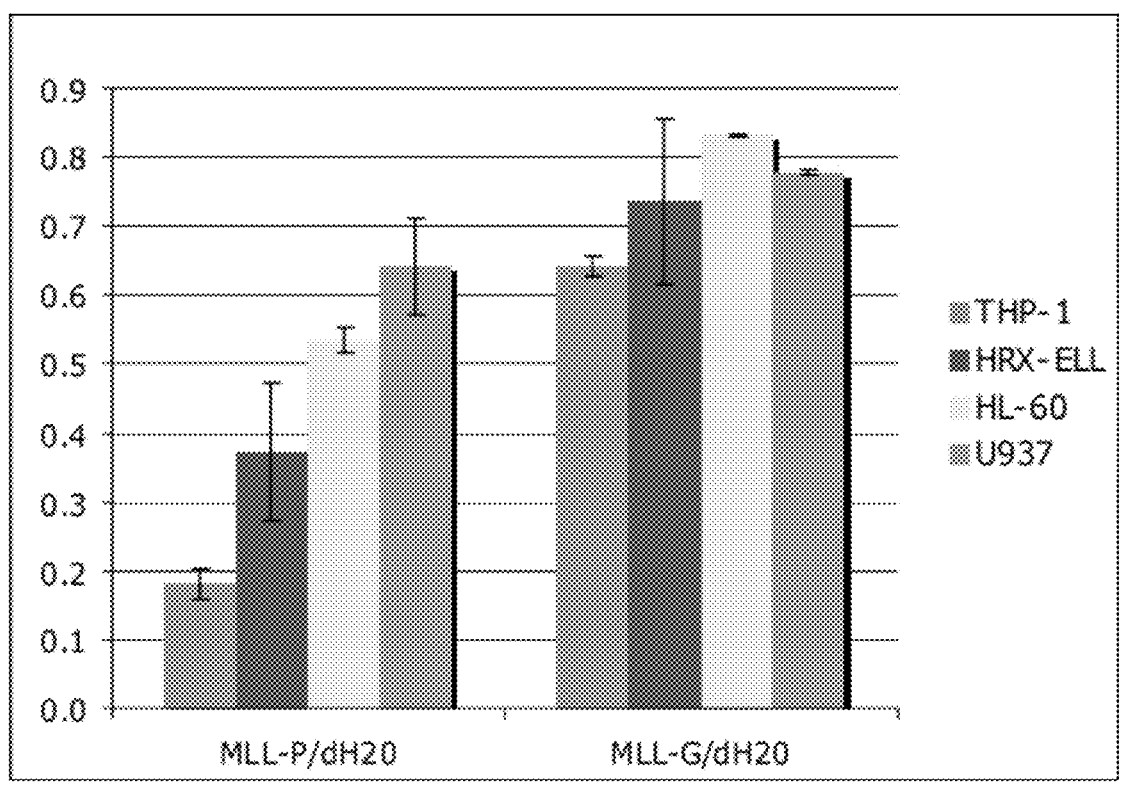

FIG. 6 shows relative growth inhibition of TAT-MLL versus TAT-MLL mutant.

DETAILED DESCRIPTION

To determine the precise domain that mediates the binding of MLL to menin, a series of peptides from the N-terminus of MLL were synthesized. To assess disruption of binding of transfected MLL to endogenous menin, a FLAG-tagged MLL 1-330 construct was transfected into 293 cells and the cell lysates were incubated with a series of peptides listed below or with water as a control. Cell lysates were immunoprecipitated with anti-FLAG antibody (Sigma), separated by SDS-PAGE and blotted with an anti-menin antibody (Bethyl Laboratories Inc. or Santa-Cruz). The amino acid numbers from the N-terminus of MLL are indicated below (preceding the amino acid sequence) for the peptides analyzed for their ability to disrupt the interaction of MLL and menin.

| Amino Acid Number | Amino Acid Sequence |
|---|---|
| 1-10 | MAHSCRWRFP (SEQ ID NO: 19) |
| 1-11 | MAHSCRWRFPA (SEQ ID NO: 20) |
| 1-12 | MAHSCRWRFPAR (SEQ ID NO: 21) |

| Amino Acid Number | Amino Acid Sequence |
|---|---|
| 1-13 | MAHSCRWRFPARP (SEQ ID NO: 1) |
| 1-14 | MAHSCRWRFPARPG (SEQ ID NO: 2) |
| 1-18 | MAHSCRWRFPARPGTTGG (SEQ ID NO: 3) |
| 1-22 | MAHSCRWRFPARPGTTGGGGGG (SEQ ID NO: 4) |
| 1-26 | MAHSCRWRFPARPGTTGGGGGGRRG (SEQ ID NO: 5) |
| 1-30 | MAHSCRWRFPARPGTTGGGGGGRRGLGGG (SEQ ID NO: 6) |
| 2-18 | AHSCRWRFPARPGTTGG (SEQ ID NO: 7) |
| 3-18 | HSCRWRFPARPGTTGG (SEQ ID NO: 8) |
| 4-18 | SCRWRFPARPGTTGG (SEQ ID NO: 9) |
| 5-18 | CRWRFPARPGTTGG (SEQ ID NO: 10) |
| 6-18 | RWRFPARPGTTGG (SEQ ID NO: 22) |
| 7-18 | WRFPARPGTTGG (SEQ ID NO: 23) |
| 8-18 | RFPARPGTTGG (SEQ ID NO: 24) |
| 2-14 | AHSCRWRFPARPG (SEQ ID NO: 11) |
| 3-14 | HSCRWRFPARPG (SEQ ID NO: 12) |
| 4-14 | SCRWRFPARPG (SEQ ID NO: 13) |
| 5-14 | CRWRFPARPG (SEQ ID NO: 14) |
| 6-14 | RWRFPARPG. (SEQ ID NO: 25) |

Figure 1:
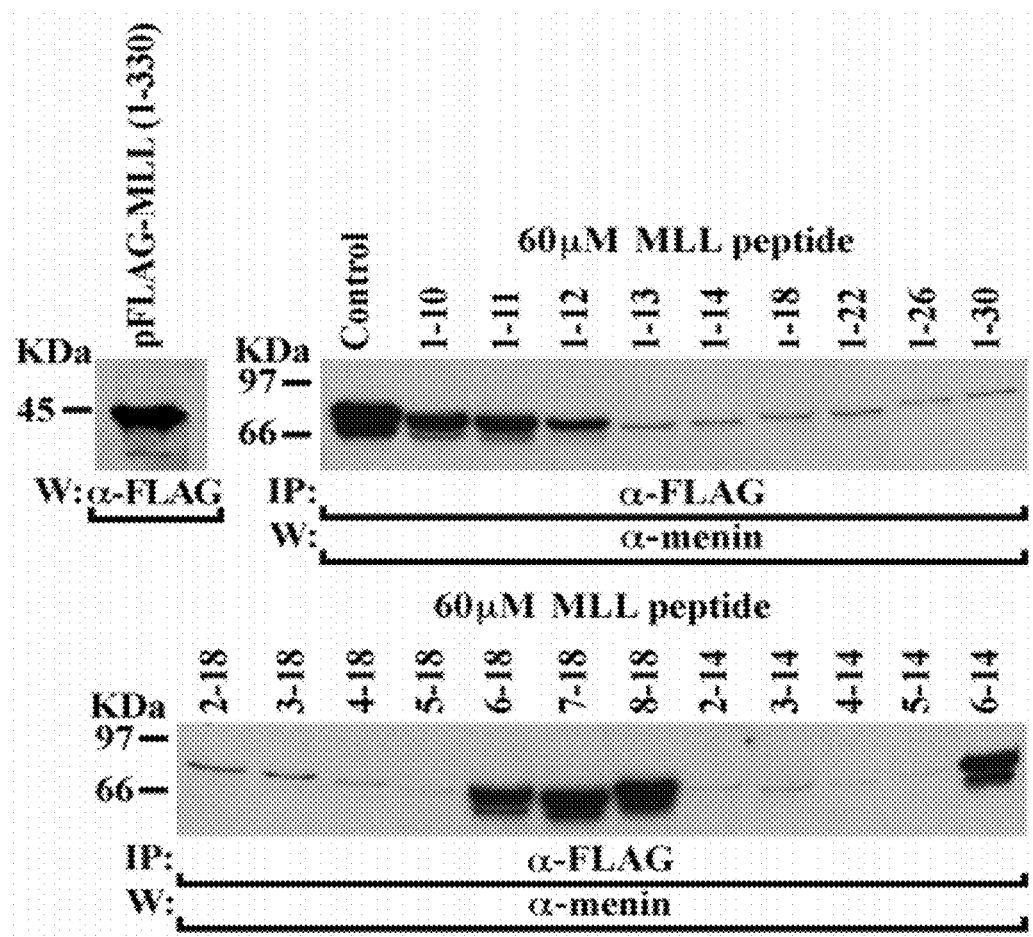
FIG. 1 is a Western blot showing that MLL peptides 1-13, 1-14, 1-18, 1-22, 1-26, 1-30, 2-18, 3-18, 4-18, 5-18, 2-14, 3-14, 4-14, and 5-14 block the interaction of transfected MLL with endogenous menin. However MLL peptides 1-10, 1-11, 1-12, 6-18, 7-18, 8-18, and 6-14 of MLL do not block the interaction of MLL with menin. These experiments demonstrate that the smallest MLL peptide that blocks the interaction of MLL with menin is MLL peptide 5-14, although 5-13 is functionally equivalent, only a Gly in position 14 is useful for synthesis.

As shown in FIG. 1, Western blot showing the interaction of transfected MLL with endogenous menin; MLL peptides 1-10, 1-11, and 1-12 do not block the interaction of MLL with menin. In contrast, an MLL peptide that begins with amino acid 1 and spans through amino acid 13, blocks the interaction with menin significantly. Peptides that include larger fragments of MLL through amino acids 30 also block the interaction with menin. However, there is no apparent difference in the degree of inhibition of the MLL-menin interaction with larger MLL peptides. To determine the amino acids that are required to block the interaction of MLL and menin, the N-terminal residues of MLL were sequentially truncated. MLL peptides that lack amino acids at positions 2, 3, 4, and 5 of MLL and span through either amino acids 18 or 14 retain the capacity to block the interaction with menin. However, deletion of amino acid 6 is sufficient to eliminate the inhibition of menin binding. These results establish that a peptide containing MLL amino acids 5-14 is sufficient to block interaction with endogenous menin and defines a critical domain as a therapeutic target in MLL-associated leukemia.

Figure 2:
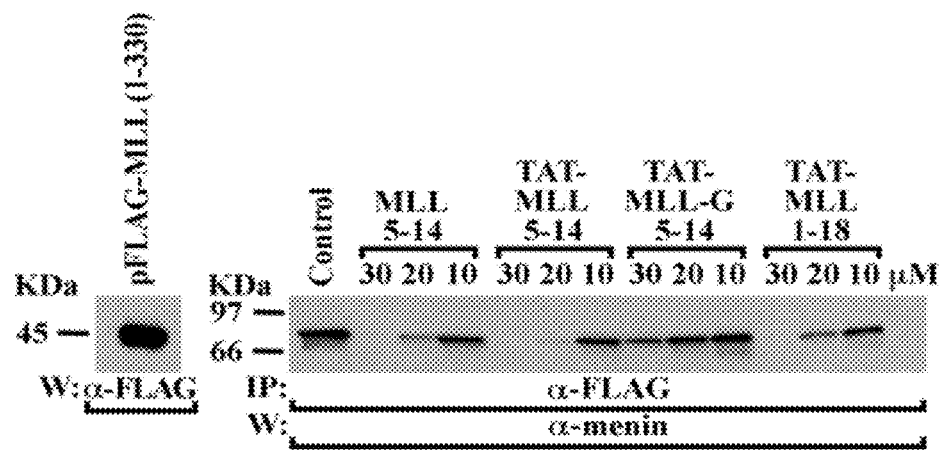
FIG. 2 is a Western blot showing effects of MLL 5-14 peptide, TAT-MLL 5-14, TAT-MLL-G 5-14, and TAT-MLL 1-18 peptides on the inhibition of menin binding. The sequence of the MLL 5-14 peptide is CRWRFPARPG (SEQ ID NO: 14). In the TAT-MLL peptide, MLL residues 5-14 are fused to the TAT domain, and this peptide contains the following sequence RKKRRQRRR-GG-CRWRFPARPG (SEQ ID NO: 15). To examine the importance of the proline residues in MLL 5-14, prolines were replaced by glycines. This peptide is referred to as TAT-MLL-G and contains the following sequence RKKRRQRRR-GG-CRWRFGARGG (SEQ ID NO: 16). The concentrations tested for each peptide were 10, 20, and 30 μM. A dose-dependent inhibition of the binding of transfected MLL 1-330 to endogenous menin with MLL 5-14, TAT-MLL 5-14, and TAT-MLL 1-18 was observed. In contrast, TAT-MLL-G 5-14 did not inhibit the binding of MLL1-330 with menin. These results show that TAT-MLL 5-14 blocks binding to menin to the same extent as MLL 5-14, indicating that the addition of the TAT domain does not interfere with the ability of MLL 5-14 to block binding to menin. However, replacement of the prolines to glycines by TAT-MLL-G 5-14 abolishes the ability of this peptide to block binding with menin, indicating that the prolines are required for menin binding. The inability of the TAT-MLL-G 5-14 to block binding to menin demonstrates the specificity of TAT-MLL 5-14 in its ability to block binding to menin. To examine whether a longer MLL peptide would have a different effect on binding TAT-MLL 1-18 was tested. This peptide contains the following sequence RKKRRQRRR-GG-MAHSCRWR-FPARPGTTGG (SEQ ID NO: 17). A similar ability of TAT-MLL 1-18 to inhibit binding to menin was observed compared to TAT-MLL 5-14, indicating that a longer MLL peptide does not increase the inhibition of binding to menin and demonstrates that TAT-MLL 5-14 is sufficient for this activity.

To determine whether the addition of the TAT domain to MLL amino acids 5-14 impacts the ability of the MLL peptide to block interaction with menin, the MLL 5-14 peptide was compared with a TAT-MLL 5-14 peptide and an equivalent inhibition of menin binding was observed (FIG. 2). To determine whether the proline residues in MLL 5-14 are necessary for menin interaction, a TAT-MLL 5-14 peptide was synthesized with prolines replaced by glycines (TAT-MLL-G 5-14) and it was observed that this peptide did not block the interaction of MLL with menin. This TAT-MLL-G 5-14 peptide is therefore useful as a control in experiments. These experiments also established a dose range between 10-30 µM for these specific TAT-MLL peptides in order to effectively block the MLL interaction with menin. The glycine at position 14 of the MLL-derived peptides was included for the purpose of ease of synthesis of synthetic peptides. Therefore, for MLL-derived peptides that have a glycine at position 14 as the C-terminal end can be deleted.

One or more amino acids are added to either the N-terminus or the C-terminus without substantially altering the function of the peptides disclosed herein. Peptides consisting essentially of the sequences disclosed herein are also within the scope of the disclosure. Some of the substitutions to the peptides disclosed herein include amino acid analogs and peptide mimetics. Peptide mimetics that have similar MLL-menin interfering function can be developed using techniques known to a skilled artisan.

Small molecules that inhibit MLL-menin binding can also be developed based on the structural information provided by the binding characteristics of the MLL-derived peptides disclosed herein. Small molecules are tested for their ability to mimic the ability of the MLL peptide to bind to menin by methods known to those of skill in the art guided by this specification.

Examples of suitable cell-permeable peptides or peptide domains include, for example, small polybasic peptides derived from the transduction domains of certain proteins, such as the third-helix of the Antennapedia (Antp) homeodomain, an RYIRS (SEQ ID NO: 26) tag sequence, Penetratin (RQIKIWFQNRRMKWKK) (SEQ ID NO: 27), Tat (GRKKRRQRRRPPQ) (SEQ ID NO: 28), Transportan (GWTLNSAGYLLGKINLKALAALAKKIL) (SEQ ID NO: 29), VP22 (DAATATRGRSAASRPTERPRAPARSASR-PRRPVD) (SEQ ID NO: 30), Amphipathic peptides (secondary and primary), MAP (KLALKLALKALKAALKLA) (SEQ ID NO: 31), KALA (WEAKLAKALAKALA-KHLAKALAKALKACEA) (SEQ ID NO: 32), ppTG20 (GLFRALLRLLRSLWRLLLRA) (SEQ ID NO: 33), Trimer (VRLPPP) (SEQ ID NO: 34), P1 (MGLGLHLLVLAAALQ-GAWSQPKKKRKV) (SEQ ID NO: 35), MPG (GALFLG-FLGAAGSTMGAWSQPKKKRKV) (SEQ ID NO: 36), Pep-1 (KETWWETWWTEWSQPKKKRKV) (SEQ ID NO: 37), Arg9 (RRRRRRRRR) (SEQ ID NO: 38), Loligomer Branched Polylysine+NLS, hCT (LGTYTQDFNKFHTF-PQTAIGVGAP) (SEQ ID NO: 39), Octa-arginine (RRRRRRRR) (SEQ ID NO: 40), Flock-house virus coat (RRRRNRTRRNRR) (SEQ ID NO: 41), HIV-1 Rev (TRQARRNRRRRWRERQR) (SEQ ID NO: 42), oligolysine, oligoarginine, proline-rich peptides, and calcitonin-derived peptides.

A dose range of about 10-30 µM or about 5-100 µM or about 1-1000 µM for MLL-derived cell-permeable peptides is suitable to block menin interaction in vivo. Administration of cell-permeable proteins or peptides can be accomplished in various ways, including intratumoral injection, infusion, and intravenous administration. A cell-permeable MLL peptide has one or more amino acids or other structural features that enable transit of the MLL peptides into a malignant cell. For example an MLL fusion peptide has a TAT cell-permeable peptide.

EXAMPLES

Example 1

Figure 3:
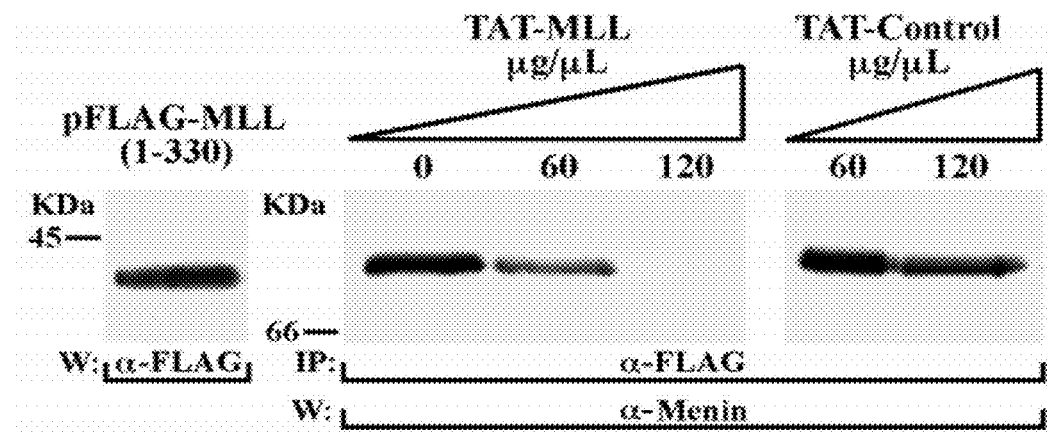
FIG. 3 is a Western blot that shows that TAT-MLL peptide specifically abrogated the menin-MLL binding whereas the TAT-scrambled control peptide did not inhibit the binding. The peptide referred to as TAT-scrambled is the best control for TAT-MLL because TAT-MLL and TAT-scrambled contain the identical amino acids. The sequence of TAT-scrambled is RKKRRQRRR-GG-RAFRPCPRWG (SEQ ID NO: 18). The amino acid composition and molecular weight of TAT-MLL and TAT-scrambled are identical. These results also confirm that the inhibition of MLL binding to menin is dose dependent.
Figure 4:
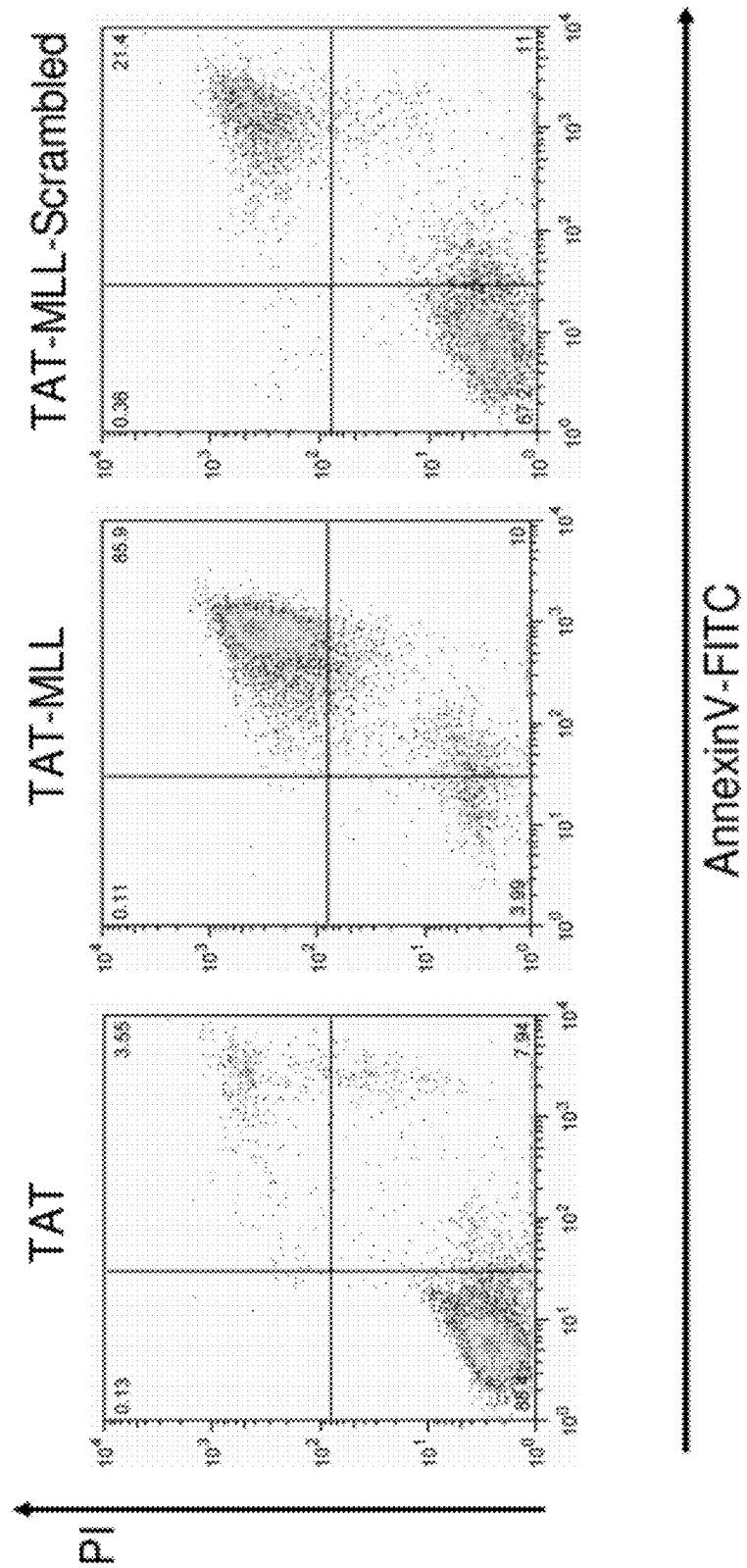
FIG. 4 shows TAT-MLL peptide induces cell death in THP-1 leukemia cells (MLL-AF9) (6 μm administered every 8 hours×6).

Development of Peptides and Small Molecules that Block the Interaction of MLL with Menin Conditional inactivation of menin results in the reversal of the transforming properties of MLL fusion proteins. A high affinity menin binding domain has been localized to the N-terminal residues of MLL, and deletion of residues 6 through 10 of MLL prevents MLL-ELL from transforming hematopoietic progenitor cells. To target the MLL-menin interaction, a series of peptides were developed for the potential to block the interaction of menin with MLL. To establish the activity of these peptides, lysates of cells transfected with FLAG-tagged N-terminal MLL sequences were examined. The lysates were immunprecipitated with a FLAG antibody, incubated with either an MLL peptide or a control scrambled peptide, and then blotted with an anti-menin antibody. A TAT-MLL peptide corresponding to the Menin interaction site inhibited the MLL-menin interaction specifically, whereas a TAT fusion containing the same residues in a scrambled sequence did not interfere with this interaction as shown in FIG. 3. To examine the activity of the TAT-MLL peptide, mouse and human leukemia cell lines were treated with the TAT-MLL peptide. The viability of MLL-ELL murine leukemia cells following treatment for 48 hours with the TAT-MLL peptide was reduced significantly compared to controls. Effects of the TAT-MLL peptide on viability of human 11q23 leukemia cell lines such as THP-1 as shown in FIG. 4. (#TIB-202, American Type Culture Collection, Manassas, Va.).

To optimize the binding affinity of the peptide, both the length of the peptide and amino acid substitutions that enhance its binding affinity are used. To increase its stability, a retro-inverso version of the TAT-MLL peptide is synthesized. To enhance release from macropinosomes, the optimized TAT-MLL peptide is fused to the HA2 domain. To target to hematopoietic cells, a DV3 ligand is used. Depending on the cell type that needs to be targeted, appropriate cell-targeting ligands can be used along with the inhibitory peptides disclosed herein.

In view of the large number of MLL protein partners, it is useful to develop a therapeutic strategy that targets the N-terminal sequence of MLL, e.g., which is conserved in all chromosome 11q23 leukemias. Additive or synergistic effects are achieved by combined targeting of binding domains within both MLL and its partner proteins. To determine whether targeting the N-terminal MLL-menin interaction exhibits synergy with blocking other partner protein interactions, the TAT-MLL is combined with the TAT-ELL and TAT-AF4 derived peptides, for possible synergistic effects.

Example 2

Treatment of Mouse Models of MLL-Associated Leukemia with TAT-MLL Alone or in Combination with the TAT-ELL and TAT-p53C' or TAT-RxL Peptides To characterize the therapeutic potential of blocking MLL-menin interaction in vivo, mouse models of MLL-ELL and MLL-AF4 leukemia are treated with the TAT-MLL peptide. MSCV-MLL-AF9, MLL-CBP, MLL-ENL, MLL-AF4 and MLL-EAF1, are used to generate mice with leukemias following retroviral transduction and transplantation. Treatment of mice with TAT-MLL combined with TAT-p53C' and TAT-RxL is contemplated.

Using the methods and compositions disclosed herein, peptides and small molecules are developed to inhibit any specific interaction of MLL and any of its binding partners. For example, MLL-derived peptides are derived for inhibiting MSCV-MLL-AF9, MLL-CBP, MLL-ENL, MLL-AF4, and MLL-EAF1 interactions. One or more of such MLL-derived peptides or equivalent small molecules can be administered in combination with other anti-neoplastic agents to obtain an additive and/or synergistic effect.

Example 3

Isolation of Small Molecule Inhibitors of MLL-Menin Interaction

In addition to peptides that inhibit the interaction of MLL with menin, a small molecule inhibitor of the MLL-menin interaction is described. Chembridge libraries (Chembridge Corp. San Diego, Calif.) are screened for small molecule inhibitors of MLL binding to menin. A screening assay includes for example, a FRET-based high-throughput assay for identifying a small molecule inhibitor for MLL-menin interaction is used. In this assay, the association of MLL with menin is reconstructed with GST-MLL and FLAG-menin, which are labeled to report their proximity by fluorescence energy transfer. Small molecules that disassociate the peptide from the protein results in a loss of 665 nm emission and are identified as a hit. Any assay to identify small molecules that interfere with the MLL-menin and other MLL-protein partners interaction is suitable.

Example 4

Figure 5:
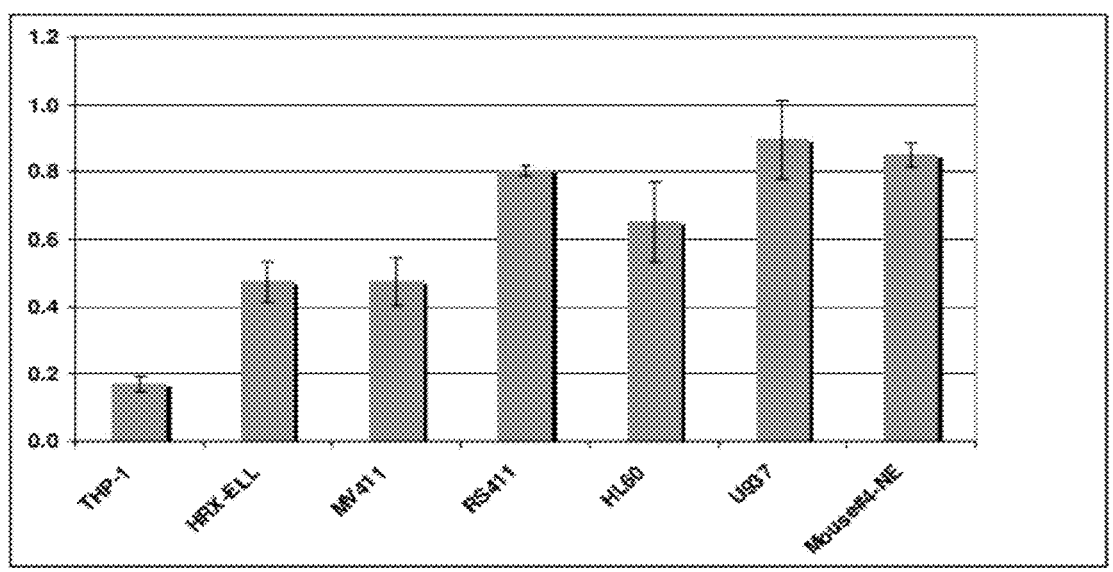
FIG. 5 shows relative growth inhibition of TAT-MLL versus scrambled in different cell lines. MLL fusion genes present in the cell lines in FIG. 5

Relative Growth Inhibition of TAT-MLL Vs. TAT-Scrambled MLL. (FIG. 5)

Leukemia cell lines were incubated with either the TAT-MLL peptide (RKKRRQRRR-GG-CRWRFPARPG) (SEQ ID NO: 15) or a scrambled control peptide consisting of TAT fused to the same 10 amino acids of MLL in a scrambled order (RKKRRQRRR-GG-RAFRPCPRWG) (SEQ ID NO: 18). The effect on growth inhibition for TAT-MLL was normalized to that of the TAT-scrambled peptide. The cell lines included: THP-1—human leukemia cell line containing MLL-AF9, HRX-ELL—mouse leukemia cell line expressing MLL-ELL and derived from a mouse model of MLL-ELL (Lavau et al., 2000), MV4;11 human leukemia cell line containing MLL-AF4 (CRL-9591, American Type Culture Collection), RS4;11 human leukemia cell line containing MLL-AF4 (CRL-1873 American Type Culture Collection), HL60 control human leukemia cell line (CCL-240, American Type Culture Collection), U937 cell line (1593-CRL, American Type Culture Collection), and Mouse #4—a leukemia cell line derived from a mouse transplanted with cells transduced with MLL-ELL that no longer expresses MLL-ELL. The Mouse #4 cell line has likely acquired additional mutations and thus no longer depends on MLL-ELL to maintain viability. Significant effects on proliferation were observed for THP-1, HRX-ELL, and MV4;11 cells, three cell lines with MLL-associated leukemia. However, RS4;11 cells exhibited more modest inhibitory effects, similar to the control cell lines HL60, U937, and Mouse #4. The scrambled peptide has the identical molecular weight and the same overall amino acid composition as TAT-MLL. However, only the TAT-MLL peptide specifically inhibits MLL-associated leukemia cell lines.

Example 5

Relative Growth Inhibition of TAT-MLL vs. TAT-MLL Mutant (FIG. 6)

Leukemia cell lines were incubated with either the TAT-MLL peptide or a control peptide consisting of TAT fused to the same 10 amino acids of MLL with the exception that the prolines were mutated to glycines (RKKRRQRRR-GG-CR-WRFGARGG (SEQ ID NO: 16). Mutation of the two prolines to glycines significantly decreases the effect of the peptide on proliferation, demonstrating the specificity of the TAT-MLL peptide. Assay is commercially available from Promega (CellTiter 96® AQueous Non-Radioactive Cell Proliferation Assay (MTS), Catalog #G5421).

Example 6

TAT-MLL Peptide Induces Cell Death in THP-1 Leukemia Cells (MLL-AF9) (6 μm, Every 8 Hours×6) (FIG. 4)

To examine the effect of TAT-MLL on cell death, THP-1 cells were treated with the either the TAT-MLL peptide or the TAT-scrambled peptide and examined by FACS analysis after 48 hours (FACScan, Becton Dickinson). Cells that are double positive for annexin V and propidium iodide (Annexin V-FITC Apoptosis Detection Kit, Catalog #556547, Becton Dickinson) have undergone cell death. 85.9% of TAT-MLL treated cells were double positive for annexin V and propidium iodide versus 21.4% of cells treated with the TAT-scrambled peptide. These results demonstrate that treatment with the TAT-MLL peptide induces cell death of the THP-1 cell line, which expresses MLL-AF9. However, the TAT-scrambled peptide has minimal effects on viability of the THP-1 cells.

Example 7

Treatment of Normal Human CD34+ Cells with TAT-MLL does not Inhibit Myeloid or Erythroid Differentiation. (Table 1)

To assess the effects of TAT-MLL peptide on hematopoiesis, normal human CD34+ cells were incubated with either the TAT-MLL peptide or the TAT-scrambled peptide at a concentration of either 7.5 μm or 10 μm. There was no effect of either the TAT-MLL peptide or the TAT-scrambled peptide on myeloid or erythroid differentiation. These results are also confirmed by FACS analysis. These results demonstrate that treatment of patients with the TAT-MLL peptide is unlikely to cause significant toxicity to normal hematopoietic cells. CD14-PE, CD15-FITC, CD71-FITC and GlyA (CD235a)-PE antibodies were obtained from Becton Dickinson Materials and Methods By "analogues" or "derivatives", a peptide is understood which, by derivatisation, substitution, preferably homologous substitution, deletion and/or insertion, is derived from the sequence of MLL and in particular from the preferred sequences disclosed herein. Conserved substitution of amino acids in the MLL-derived peptides disclosed herein can be made by a skilled artisan based on the disclosure and guidance provided herein.

Variants of polypeptides that retain a biological activity of the disclosed peptides include for example, polypeptides that are substantially homologous to MLL, but which have an amino acid sequence different from that of MLL because of one or more deletions, insertions or substitutions. Particular embodiments include, but are not limited to, MLL-derived polypeptides that comprise from one to ten deletions, insertions or substitutions of amino acid residues, when compared to a native MLL sequence. Included as variants of MLL polypeptides are those variants that are naturally occurring, such as allelic forms and alternatively spliced forms, as well as variants that have been constructed by modifying the amino acid sequence of a MLL polypeptide or the nucleotide sequence of a nucleic acid encoding a MLL polypeptide.

Generally, substitutions for one or more amino acids present in the native polypeptide should be made conservatively. Examples of conservative substitutions include substitution of amino acids outside of the active domain(s), and substitution of amino acids that do not alter the secondary and/or tertiary structure of MLL. Additional examples include substituting one aliphatic residue for another, such as Ile, Val, Leu, or Ala for one another, or substitutions of one polar residue for another, such as between Lys and Arg; Glu and Asp; or Gln and Asn. Other such conservative substitutions, for example, substitutions of entire regions having similar hydrophobicity characteristics, are known in the art. When a deletion or insertion strategy is adopted, the potential effect of the deletion or insertion on biological activity must be considered. Subunits of the inventive polypeptides may be constructed by deleting terminal or internal residues or sequences. Additional guidance as to the types of mutations that can be made is provided by a comparison of the sequence of MLL to polypeptides that have similar structures, as well as by performing structural analysis of the inventive polypeptides.

Some of the cell lines include for example:

THP-1, MV411, and RS411.

HRX-ELL—MLL-ELL (this is derived from a mouse model of MLL-ELL leukemia generated in the inventor's laboratory)

HL60—No MLL fusion. This cell line is a control.

U937—MLL-AF10—This cell line has CALM-AF10 (not MLL-AF10). This cell line is a control.

Mouse#4-NE—This cell line is derived from a mouse that received a transplant of bone marrow cells transduced with MLL-ELL. However, this cell line was observed to no longer express MLL-ELL. using two techniques: 1) immunofluorescence staining with antibodies to ELL and 2) RT-PCR for the MLL-ELL mRNA. Because the Mouse #4-NE cell lines do not express MLL-ELL, it is not responding to the TAT-MLL peptide. Thus, the Mouse #4-NE cell line is a good control for evaluating the response of expected MLL-associated leukemia cells to the TAT-MLL peptide.

The CD14-PE, CD15-FITC, CD71-FITC and GlyA-PE antibodies are commercially available.

TABLE 1

| Day 10 Erythroid Differentiation | | | | | |
|---|---|---|---|---|---|
| Treatment | Viability (%) | % of CD71−/ GlyA+ | % of CD71+/ GlyA+ | % of CD71−/ GlyA− | % of CD71+/ GlyA− |
| None | 95 | 0.11 | 75.9 | 14.6 | 9.43 |
| TAT-Scram. 10 μl | 91 | 0.11 | 75.9 | 13.1 | 10.9 |
| TAT-Scram. 7.5 μl | 96 | 0.95 | 74.6 | 11.5 | 13.0 |
| TAT-MLL 10 μl | 90 | 0.41 | 71.7 | 14.7 | 13.1 |
| TAT-MLL 7.5 μl | 90 | 0.63 | 71.2 | 14.8 | 13.4 |

| Day 10 Myeloid Differentiation | | | | | |
|---|---|---|---|---|---|
| Treatment | Viability (%) | % of CD15−/ CD14+ | % of CD15+/ CD14+ | % of CD15−/ CD14− | % of CD15+/ CD14− |
| None | 96 | 0.50 | 0.71 | 59.6 | 39.2 |
| TAT-Scram. 10 μl | 93 | 0.59 | 0.93 | 55.4 | 43.1 |

TABLE 1-continued

| | | | | | |
|---|---|---|---|---|---|
| TAT-Scram. 7.5 µl | 93 | 0.48 | 0.73 | 55.8 | 43.0 |
| TAT-MLL 10 µl | 94 | 0.45 | 0.75 | 55.9 | 42.9 |

TABLE 1-continued

| | | | | | |
|---|---|---|---|---|---|
| TAT-MLL 7.5 µl | 96 | 0.53 | 0.85 | 55.4 | 43.2 |

SEQUENCE LISTING

<160> NUMBER OF SEQ ID NOS: 43

<210> SEQ ID NO 1
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Met Ala His Ser Cys Arg Trp Arg Phe Pro Ala Arg Pro
1               5                   10

<210> SEQ ID NO 2
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Met Ala His Ser Cys Arg Trp Arg Phe Pro Ala Arg Pro Gly
1               5                   10

<210> SEQ ID NO 3
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Met Ala His Ser Cys Arg Trp Arg Phe Pro Ala Arg Pro Gly Thr Thr
1               5                   10                  15

Gly Gly

<210> SEQ ID NO 4
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Met Ala His Ser Cys Arg Trp Arg Phe Pro Ala Arg Pro Gly Thr Thr
1               5                   10                  15

Gly Gly Gly Gly Gly Gly
            20

<210> SEQ ID NO 5
<211> LENGTH: 26
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 5

Met Ala His Ser Cys Arg Trp Arg Phe Pro Ala Arg Pro Gly Thr Thr
1               5                   10                  15

Gly Gly Gly Gly Gly Gly Gly Arg Arg Gly
            20                  25

<210> SEQ ID NO 6
<211> LENGTH: 30
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Met Ala His Ser Cys Arg Trp Arg Phe Pro Ala Arg Pro Gly Thr Thr
1               5                   10                  15

Gly Gly Gly Gly Gly Gly Gly Arg Arg Gly Leu Gly Gly Gly
            20                  25                  30

<210> SEQ ID NO 7
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Ala His Ser Cys Arg Trp Arg Phe Pro Ala Arg Pro Gly Thr Thr Gly
1               5                   10                  15

Gly

<210> SEQ ID NO 8
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

His Ser Cys Arg Trp Arg Phe Pro Ala Arg Pro Gly Thr Thr Gly Gly
1               5                   10                  15

<210> SEQ ID NO 9
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Ser Cys Arg Trp Arg Phe Pro Ala Arg Pro Gly Thr Thr Gly Gly
1               5                   10                  15

<210> SEQ ID NO 10
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Cys Arg Trp Arg Phe Pro Ala Arg Pro Gly Thr Thr Gly Gly
1               5                   10

<210> SEQ ID NO 11
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Ala His Ser Cys Arg Trp Arg Phe Pro Ala Arg Pro Gly
1               5                   10

<210> SEQ ID NO 12
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

His Ser Cys Arg Trp Arg Phe Pro Ala Arg Pro Gly
1               5                   10

<210> SEQ ID NO 13
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Ser Cys Arg Trp Arg Phe Pro Ala Arg Pro Gly
1               5                   10

<210> SEQ ID NO 14
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Cys Arg Trp Arg Phe Pro Ala Arg Pro Gly
1               5                   10

<210> SEQ ID NO 15
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Arg Lys Lys Arg Arg Gln Arg Arg Gly Gly Cys Arg Trp Arg Phe
1               5                   10                  15

Pro Ala Arg Pro Gly
            20

```
<210> SEQ ID NO 16
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Arg Lys Lys Arg Arg Gln Arg Arg Gly Gly Cys Arg Trp Arg Phe
1               5                   10                  15

Gly Ala Arg Gly Gly
            20

<210> SEQ ID NO 17
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Arg Lys Lys Arg Arg Gln Arg Arg Gly Gly Met Ala His Ser Cys
1               5                   10                  15

Arg Trp Arg Phe Pro Ala Arg Pro Gly Thr Thr Gly Gly
            20                  25

<210> SEQ ID NO 18
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Arg Lys Lys Arg Arg Gln Arg Arg Gly Gly Arg Ala Phe Arg Pro
1               5                   10                  15

Cys Pro Arg Trp Gly
            20

<210> SEQ ID NO 19
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Met Ala His Ser Cys Arg Trp Arg Phe Pro
1               5                   10

<210> SEQ ID NO 20
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Met Ala His Ser Cys Arg Trp Arg Phe Pro Ala
1               5                   10

<210> SEQ ID NO 21
```

```
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Met Ala His Ser Cys Arg Trp Arg Phe Pro Ala Arg
1               5                   10

<210> SEQ ID NO 22
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Arg Trp Arg Phe Pro Ala Arg Pro Gly Thr Thr Gly Gly
1               5                   10

<210> SEQ ID NO 23
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Trp Arg Phe Pro Ala Arg Pro Gly Thr Thr Gly Gly
1               5                   10

<210> SEQ ID NO 24
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Arg Phe Pro Ala Arg Pro Gly Thr Thr Gly Gly
1               5                   10

<210> SEQ ID NO 25
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Arg Trp Arg Phe Pro Ala Arg Pro Gly
1               5

<210> SEQ ID NO 26
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Arg Tyr Ile Arg Ser
```

```
<210> SEQ ID NO 27
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Arg Gln Ile Lys Ile Trp Phe Gln Asn Arg Arg Met Lys Trp Lys Lys
1               5                   10                  15

<210> SEQ ID NO 28
<211> LENGTH: 13
<212> TYPE: PRT
<213> ORGANISM: Human immunodeficiency virus 1

<400> SEQUENCE: 28

Gly Arg Lys Lys Arg Arg Gln Arg Arg Arg Pro Pro Gln
1               5                   10

<210> SEQ ID NO 29
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 30
<211> LENGTH: 34
<212> TYPE: PRT
<213> ORGANISM: Human herpesvirus 1

<400> SEQUENCE: 30

Asp Ala Ala Thr Ala Thr Arg Gly Arg Ser Ala Ser Arg Pro Thr
1               5                   10                  15

Glu Arg Pro Arg Ala Pro Ala Arg Ser Ala Ser Arg Pro Arg Arg Pro
            20                  25                  30

Val Asp

<210> SEQ ID NO 31
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Lys Leu Ala Leu Lys Leu Ala Leu Lys Ala Leu Lys Ala Ala Leu Lys
1               5                   10                  15

Leu Ala

<210> SEQ ID NO 32
<211> LENGTH: 30
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 32

Trp Glu Ala Lys Leu Ala Lys Ala Leu Ala Lys Ala Leu Ala Lys His
1               5                   10                  15

Leu Ala Lys Ala Leu Ala Lys Ala Leu Lys Ala Cys Glu Ala
            20                  25                  30

<210> SEQ ID NO 33
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Gly Leu Phe Arg Ala Leu Leu Arg Leu Leu Arg Ser Leu Trp Arg Leu
1               5                   10                  15

Leu Leu Arg Ala
            20

<210> SEQ ID NO 34
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Val Arg Leu Pro Pro Pro
1               5

<210> SEQ ID NO 35
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Met Gly Leu Gly Leu His Leu Leu Val Leu Ala Ala Ala Leu Gln Gly
1               5                   10                  15

Ala Trp Ser Gln Pro Lys Lys Lys Arg Lys Val
            20                  25

<210> SEQ ID NO 36
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Gly Ala Leu Phe Leu Gly Phe Leu Gly Ala Ala Gly Ser Thr Met Gly
1               5                   10                  15

Ala Trp Ser Gln Pro Lys Lys Lys Arg Lys Val
            20                  25

<210> SEQ ID NO 37
```

<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 37

Lys Glu Thr Trp Trp Glu Thr Trp Trp Thr Glu Trp Ser Gln Pro Lys
1               5                   10                  15

Lys Lys Arg Lys Val
            20

<210> SEQ ID NO 38
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 38

Arg Arg Arg Arg Arg Arg Arg Arg Arg
1               5

<210> SEQ ID NO 39
<211> LENGTH: 24
<212> TYPE: PRT
<213> ORGANISM: Artificial Sequence
<220> FEATURE:
<223> OTHER INFORMATION: Description of Artificial Sequence: Synthetic peptide

<400> SEQUENCE: 39

Leu Gly Thr Tyr Thr Gln Asp Phe Asn Lys Phe His Thr Phe Pro Gln
1               5                   10                  15

Thr Ala Ile Gly Val Gly Ala Pro
            20

<210> SEQ ID NO 40
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 40

Arg Arg Arg Arg Arg Arg Arg Arg
1               5

<210> SEQ ID NO 41
<211> LENGTH: 12
<212> TYPE: PRT
<213> ORGANISM: Flock house virus

<400> SEQUENCE: 41

Arg Arg Arg Arg Asn Arg Thr Arg Arg Asn Arg Arg
1               5                   10

<210> SEQ ID NO 42
<211> LENGTH: 17
<212> TYPE: PRT
<213> ORGANISM: Human herpesvirus 1

<400> SEQUENCE: 42

Thr Arg Gln Ala Arg Arg Asn Arg Arg Arg Arg Trp Arg Glu Arg Gln

```
                1               5                  10                 15
Arg

<210> SEQ ID NO 43
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Arg Lys Lys Arg Arg Gln Arg Arg Arg
1               5
```

The invention clamed is:

1. A method of inducing cell death in a malignant hematological cell that exhibits a detectable MLL gene arrangement or an MLL fusion protein, the method comprising:
   a. providing a peptide that disrupts the interaction of mixed-lineage leukemia (MLL) and menin, wherein the peptide is capable of interfering with MLL protein binding to menin through a binding region of MLL, the MLL protein comprising an amino acid sequence CRWRFPARPG (SEQ ID NO: 14); and
   b. inducing cell death in the malignant cell.

2. The method of claim 1, wherein the peptide is provided in a concentration of about 1 to about 1000 μM.

3. The method of claim 1, wherein the peptide is provided in a concentration of about 5 to about 100 μM.

4. The method of claim 1, wherein the peptide is provided in a concentration of about 10 to about 30 μM.

5. The method of claim 1, wherein the peptide is delivered intraveneously.

6. The method of claim 1, wherein the peptide is delivered by infusion.

* * * * *

UNITED STATES PATENT AND TRADEMARK OFFICE
CERTIFICATE OF CORRECTION

| | | |
|---|---|---|
| PATENT NO. | : 8,557,778 B2 | Page 1 of 1 |
| APPLICATION NO. | : 13/552126 | |
| DATED | : October 15, 2013 | |
| INVENTOR(S) | : Michael J. Thirman | |

It is certified that error appears in the above-identified patent and that said Letters Patent is hereby corrected as shown below:

In the Claims

Please amend claim 1 as follows:

col. 27, line 21, delete the word "arrangement" and insert in its place the word
--rearrangement--

Signed and Sealed this
Fourth Day of February, 2014

Michelle K. Lee
*Deputy Director of the United States Patent and Trademark Office*